(12) United States Patent
Takada (10) Patent No.: US 7,649,625 B2
(45) Date of Patent: Jan. 19, 2010

(54) OPTICAL APPARATUS, PHOTOMASK INSPECTING APPARATUS, AND EXPOSURE APPARATUS

(75) Inventor: Akira Takada, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 12/412,825

(22) Filed: Mar. 27, 2009

(65) Prior Publication Data

US 2009/0244531 A1 Oct. 1, 2009

(30) Foreign Application Priority Data

Mar. 28, 2008 (JP) ............................. 2008-085607

(51) Int. Cl.
*G01N 21/00* (2006.01)
*G03B 27/54* (2006.01)

(52) U.S. Cl. ................... 356/237.5; 356/400; 355/53; 355/55; 355/67; 355/30

(58) Field of Classification Search ... 356/237.2–237.5, 356/399–401; 355/30, 50, 53, 55, 67; 430/5, 430/30, 311, 396; 250/372, 428, 397
See application file for complete search history.

(56) References Cited

U.S. PATENT DOCUMENTS

| 4,668,077 | A * | 5/1987 | Tanaka ........................ 355/30 |
| 5,474,864 | A | 12/1995 | Isao et al. |
| 6,235,438 | B1 * | 5/2001 | Suzuki et al. ................. 430/30 |
| 6,331,885 | B1 * | 12/2001 | Nishi ........................... 355/53 |
| 6,667,796 | B1 * | 12/2003 | Nishi ........................... 355/30 |
| 6,750,951 | B2 * | 6/2004 | Koyama et al. ............... 355/67 |
| 6,811,953 | B2 * | 11/2004 | Hatada et al. ............... 430/311 |
| 2003/0227607 | A1 * | 12/2003 | Kato et al. .................... 355/53 |

FOREIGN PATENT DOCUMENTS

| JP | 04-136854 | 5/1992 |
| JP | 11-072905 | 3/1999 |

* cited by examiner

*Primary Examiner*—Sang Nguyen
(74) *Attorney, Agent, or Firm*—Brinks Hofer Gilson & Lione (57) ABSTRACT

An optical apparatus includes a laser light source for emitting a beam of light, an integrator for dividing the beam of light into plural beams of light, and a light focusing optical system for focusing the beams of light passed through the integrator. The optical apparatus also includes a stage, on which the light concentrated by the light focusing optical system is irradiated and on which an object may be placed, and includes a projecting optical system for projecting the light transmitted through the object. The following conditions satisfy the following numerical formula (1). The projecting optical system has a visual field including an effective visual field, and the integrator has a division number N corresponding to a predetermined direction in a predetermined effective visual field. A ghost image is formed in the effective visual field in the predetermined direction and has contrast γ. The light focusing optical system has numerical aperture $NA_1$, the projecting optical system has numerical aperture $NA_2$, and $(NA_1/NA_2)$ defines a coherence factor σ. The object has a light blocking portion with an amplitude transmittance T.

$$N \geq \frac{\sigma}{\pi} \sqrt[3]{\frac{8}{\pi C^2}} \quad (C = \gamma/T) \quad (1)$$

4 Claims, 6 Drawing Sheets

OPTICAL APPARATUS, PHOTOMASK INSPECTING APPARATUS, AND EXPOSURE APPARATUS

RELATED APPLICATIONS

This application claims priority under 35 U.S.C. §119 to Japanese Patent Application No. JP2008-085607 filed on Mar. 28, 2008, the entire content of which is hereby incorporated by reference.

BACKGROUND OF THE INVENTION

1. Technical Field

The present invention relates to a technique that may be used in apparatuses for detecting pattern defects in photomasks used in photolithography processes. In particular, the present invention relates to a technique for reducing the effects of ghost images that may occur when a laser is used as a light source.

2. Background Art

As an inspecting apparatus used in a semiconductor manufacturing process, an apparatus for inspecting pattern defects in a photomask (reticle) may be used. This apparatus includes an illuminating optical system for illuminating a photomask and includes a sensor for detecting an image of the photomask and outputting a signal of the image, and a pattern of the mask is thereby inspected based on the signal of the image that is output.

Recently, as patterns in semiconductor devices are made finer, the importance of inspecting a mask of a base form of a circuit pattern has been increasing. While a wavelength of illuminating light must be shortened in order to detect microdefects, a laser light source such as an ultraviolet laser may be used in view of the size of the apparatus and efficiency. Since laser light is highly coherent, when the laser light is used as a light source in a defect inspecting apparatus, interference occurs, and ghost images (multiple images generated at a place other than at the proper location) may be generated in a detected image output from a sensor. In addition, when a laser light source is used, the distribution of luminance of the laser light on an illuminated surface (or image intensity) may be uneven, which is undesirable.

The above-described ghost image does not have negative effects in the case of a binary mask, in which light and dark can be clearly distinguished, but does have negative effects in a case of a phase-shift mask (also called a "halftone mask"). Specifically, the ghost image will be a hindrance in the inspection of pattern defects of a mask.

For example, in an attenuated phase-shift mask, a masked area (an area that is not open) has a transmittance of several % to several tens of % with respect to a transmission area (an open area), and the masked area rotates the phase of the exposure light by 180 degrees. According to this function, edges of a pattern are clearly formed, whereby an even finer circuit pattern can be formed. An attenuated phase-shift mask is disclosed in Japanese Patent Application Laid-Open No. 4-136854 and Japanese Patent Application Laid-Open No. 7-140635, for example. The masked area of the attenuated phase-shift mask may transmit some amount of light, and it is thereby called a "halftone area".

Since laser light is highly coherent, when the laser light is used as an illuminating light for a phase-shift mask, light that is transmitted through an open area of the mask and light that is partially transmitted through a halftone area interfere with each other. As a result, interference fringes are generated and are found to be the above-described ghost images. Even when the ghost image is not generated, fine fringes overlap each other, thereby generating an uneven intensity distribution (an uneven luminance distribution) of light transmitted through the photomask.

A technique for reducing the generation of the ghost images is proposed in Japanese Patent Application Laid-Open No. 11-72905, for example. In this technique, laser light is emitted from a light source and is passed through an integrator (a fly-eye lens) and a rotating phase plate so that the phase of the laser light is randomly changed, whereby temporal coherence is decreased. In Japanese Patent Application Laid-Open No. 11-72905, as a technique for decreasing effects of an uneven luminance distribution, a technique for evening out deviation of the luminance distribution by using an oscillating mirror is disclosed.

SUMMARY OF THE INVENTION

However, even when the above-described techniques are used, it is difficult to reduce the generation of the ghost images to such a degree that the effects of the ghost images are negligible. The present inventor has theoretically analyzed this point and has found the following. That is, in the above-described techniques, the effect of the temporal coherence is reduced, whereas an effect of spatial coherence is not decreased. Therefore, interference occurs by spatial coherence of laser light in using a phase-shift mask, whereby ghost images are generated. The present invention is based on this finding and has as an object to provide a technique for reducing generation of ghost images by spatial coherence.

According to a first aspect of the present invention, the present invention provides an optical apparatus including a laser light source for emitting a beam of light, an integrator for dividing the beam of light into plural beams of light, and a light focusing optical system for focusing the beams of light passed through the integrator. The optical apparatus also includes a stage, on which the light concentrated by the light focusing optical system is irradiated and on which an object may be placed, and includes a projecting optical system for projecting the light transmitted through the object. The following conditions satisfy the following numerical formula (1). The projecting optical system has a visual field including an effective visual field, and the integrator has a division number N corresponding to a predetermined direction in a predetermined effective visual field. A ghost image is formed in the effective visual field in the predetermined direction and has contrast γ. The light focusing optical system has numerical aperture $NA_1$, the projecting optical system has numerical aperture $NA_2$, and $(NA_1/NA_2)$ defines a coherence factor σ. The object has a light blocking portion with an amplitude transmittance T.

$$N \geq \frac{\sigma}{\pi} \sqrt[3]{\frac{8}{\pi C^2}} \quad (C = \gamma/T) \tag{1}$$

According to the first aspect of the present invention, when a threshold value of acceptable contrast of a ghost image is expressed as γ, the contrast of a ghost image generated in the effective visual field will be not more than γ. That is, a condition for decreasing luminance of a ghost image in the effective visual field so as to be not more than the acceptable value is obtained.

For example, in an apparatus for inspecting defects of a photomask by image analysis, a ghost image may not be a hindrance to detection of defects so long as the contrast value of the ghost image is not more than γ. In this case, by selecting N so as to satisfy the numerical formula (1), the detection of defects of the photomask is performed with no difficulty even when a ghost image is generated. A derivation process of the numerical formula (1) will be described in detail in the embodiment.

According to the first aspect of the present invention, a luminance distribution of laser light in the effective visual field is made even, whereby the evenness of an intensity distribution is improved. A ghost image is a principal maximum of an interference, and a plurality of a subsidiary maximum (secondary, tertiary . . . n-th order interference image) is formed close to the ghost image. These high order interferences have low intensities as images, but still have intensity distributions of light, thereby causing unevenness in the intensity distribution of light that passed through a photomask, by overlapping others. Accordingly, by decreasing the intensity of the image of the principal maximum, the effects of the above-described subsidiary maximum in the effective visual field are decreased. That is, the unevenness of the light intensity distribution due to the above-described subsidiary maximum is improved.

The contrast value γ of a ghost image is calculated by (light intensity of a ghost image/light intensity of a real image)× 100%. As a laser light source, a laser oscillator for continuous wave oscillation is suitably used. In addition, a laser oscillator for pulsed oscillation may be used. The beam of the first aspect of the present invention may be a beam of light consisting of one light flux, such as a laser beam emitted from one lens. Alternately, plural laser light sources may be used, and the beam may be a beam of light consisting of overlapped light fluxes emitted from these light sources.

In the case of using plural laser light sources, the number of the light sources is included in N. For example, when the number of the laser light sources is 2×2=4, and the number of integrators is 4×4=16, the division number is 4×16=64, and optical effects are obtained. The optical effects are the same as those in a case in which a beam of light consisting of one light flux is passed through integrators of 8×8=64.

The integrator has a lens structure, in which plural lens systems are arranged in parallel in a matrix state, and makes light emitted from the light source be approximately parallel. That is, light flux entering into the integrator is divided by the lens systems arranged in a matrix state (grid state), whereby plural two-dimensional images of the light source are formed. Light fluxes are emitted from these plural two-dimensional images of the light source and overlap each other on an illuminated surface, and the same condition as that in a case of parallel light irradiation is obtained.

As an integrator, an integrator using a fly-eye lens is generally used, and a microlens array may be used instead of the fly-eye lens. The fly-eye lens may be formed by physically combining plural lens systems together and can be produced at relatively low cost compared to the microlens array. The fly-eye lens includes optical effects at boundary portions between adjacent integrator elements (single lenses), and the optical effects are not negligible. The microlens array has one body in which plural lens structures are formed in a matrix state on a surface (and/or a back surface) of one light transmissive member. The light transmissive member may be a plastic plate or a silica glass plate, for example. When a microlens array is made of a material, for example, a silica, processing cost is high, and the production cost will be high for a microlens array for ultraviolet light. In this case, the microlens array has an advantage that the above-described optical effects at the boundary portions between the adjacent integrator elements (single lenses) do not occur. For an integrator, a required division number is secured by serially arranging plural lens systems.

The light focusing optical system functions as an illuminating optical system and is an optical system which focuses laser light emitted from the integrator and illuminates an object with the laser light. The simplest light focusing optical system is made of one light focusing lens. The light focusing optical system may be formed by using plural lenses.

The object may be a photomask used in a photolithography process, for example. The photomask is also called a "reticle" in the field of LSI photolithography, and a "photomask" in the present description corresponds to both cases. The object is not limited to the photomask. For example, the object of the present invention may be a sample for inspecting a surface condition, an inside condition, or impurities of the material by transmitting laser light therethrough and detecting the transmitted light.

The stage is a member that is used for mounting the object to the optical apparatus. Although it is expressed as a "stage", the stage is not limited to a stand structure, and any member that can hold the object may be used.

The projecting optical system has a function that is converse to the function of the light focusing optical system. That is, the light concentrated by the light focusing optical system is irradiated on the object, and the light is transmitted through the object and is scattered again. The projecting optical system condenses this scattered light flux and transmits this light to the subsequent sensor system. The simplest projecting optical system is made of one focusing lens, as in the case of the light focusing optical system. The projecting optical system may be made of plural lenses.

The effective visual field is within the visual field of the projecting optical system and is a visual field which is a part of a visual field recognized at the projecting optical system and is practically used in observation. For example, when a photomask is used as an object, and defects of the photomask are inspected by using an image recognized at the projecting optical system, a field for the base of an image for detecting the defects is used as an effective visual field. In other words, a field, at which the image for detecting the defects of the photomask is obtained, is used as an effective visual field. Accordingly, there may be a case of having a field within a visual field recognized at the projecting optical system and at the outside of an effective visual field. In this case, the field at the outside of the effective visual field is not used for detecting defects of a photomask. In addition, there may be a case in which a field recognized at the projecting optical system coincides with an effective visual field.

The division number (N) of the integrator corresponding to a predetermined direction in the effective visual field is a division number of the integrator (for example, a division number of a fly-eye lens) in a predetermined direction crossing the effective visual field. For example, when an effective visual field has a square shape, and a division number of the integrator is n×n pieces according to the square shape of the effective visual field, a division number N of the integrator in a direction parallel to a side of the square shape is n pieces. A division number N in a diagonal direction of the square shape is a square root of n. When n is not a natural number, a natural number at the next higher level may be used. For example, when a calculated division number is 2.23 . . . , a division number N=3 is used.

The coherence factor σ is a parameter expressed by a equation having a numerical aperture of the projecting optical system as a denominator and a numerical aperture of the light focusing optical system as a numerator, and the coherence factor indicates coherency of light emitted from the illuminating optical system. For example, light having low coherency is emitted from the illuminating optical system when σ approaches infinity, and light having high coherency is emitted from the illuminating optical system when σ approaches zero.

According to a second aspect of the present invention, in the first aspect of the present invention, the following conditions satisfy the following numerical formula (2). The integrator has an aperture size D and a focal length f, and the light passing through the integrator has a wavelength λ, whereby a Fresnel number Q is defined as $D^2/(4\lambda f)=Q$ ($Q \geqq 1$). The effective visual field has a size d in the predetermined direction.

$$(2 \times d \times NA_2 \times \sigma)/(4 \times \lambda \times Q) \geqq N \geqq \frac{\sigma}{\pi} \sqrt[3]{\frac{8}{\pi C^2}} \quad (2)$$

In the second aspect of the present invention, the size d in the predetermined direction of the effective visual field is a size of the effective visual field in a direction of counting the above division number N. The inequality in the right side in the numerical formula (2) is the numerical formula (1). The inequality in the left side in the numerical formula (2) defines an upper limit of the division number of the integrator. When an integrator is used in the ultraviolet such that the wavelength is not more than 300 nm, the upper limit of the division number of the integrator is approximately 10×10. The upper limit depends on the processing accuracy of silica used as a raw material. As a method for increasing a division number of an integrator, a method for serially arranging an integrator may be used. In this method, for example, integrators having a division number of 5×5 are stacked into two layers in order to obtain effects equivalent to that in a case of using an integrator having a division number of 25×25.

As the division number of the integrator is increased, the Fresnel number of each lens element of the integrator is decreased, whereby the light concentrating effect of the lens elements is reduced, and effects of boundaries of lens elements of the integrator are increased. Therefore, the effect of increasing the division number is limited. That is, the division number of the integrator cannot be greatly increased, and there is an upper limit in practical use. The inequality in the left side in the numerical formula (2) defines the upper limit.

In a case of obtaining a predetermined division number by serially arranging plural integrators, optical design may be performed based on the following design guide. In this case, first, optical design is performed by assuming use of one integrator, and an upper limit of a division number N of the integrator is calculated by using the inequality in the left side in the above numerical formula (2). Next, a division number N satisfying the above numerical formula (2) is selected within the above upper limit, and a combination of plural integrators is selected so as to obtain a division number for satisfying the division number N. Thus, the effects of ghost images are reduced without greatly increasing the production cost.

According to a third aspect of the present invention, the present invention provides a photomask inspecting apparatus having the structure of the optical apparatus of the first aspect of the present invention. According to the third aspect of the present invention, a photomask inspecting apparatus, in which the effects of ghost images are reduced, or ghost images do not have an effect, is obtained.

According to a fourth aspect of the present invention, the present invention provides an exposure apparatus having the structure of the optical apparatus of the first aspect of the present invention. According to the fourth aspect of the present invention, an exposure apparatus, in which the effects of ghost images are reduced, or ghost images do not have an effect, is obtained.

According to the present invention, a technique for reducing the generation of ghost images due to spatial coherence is obtained.

DETAILED DESCRIPTION OF THE PREFERRED EMBODIMENTS (1) First Embodiment

Structure

Figure 1:
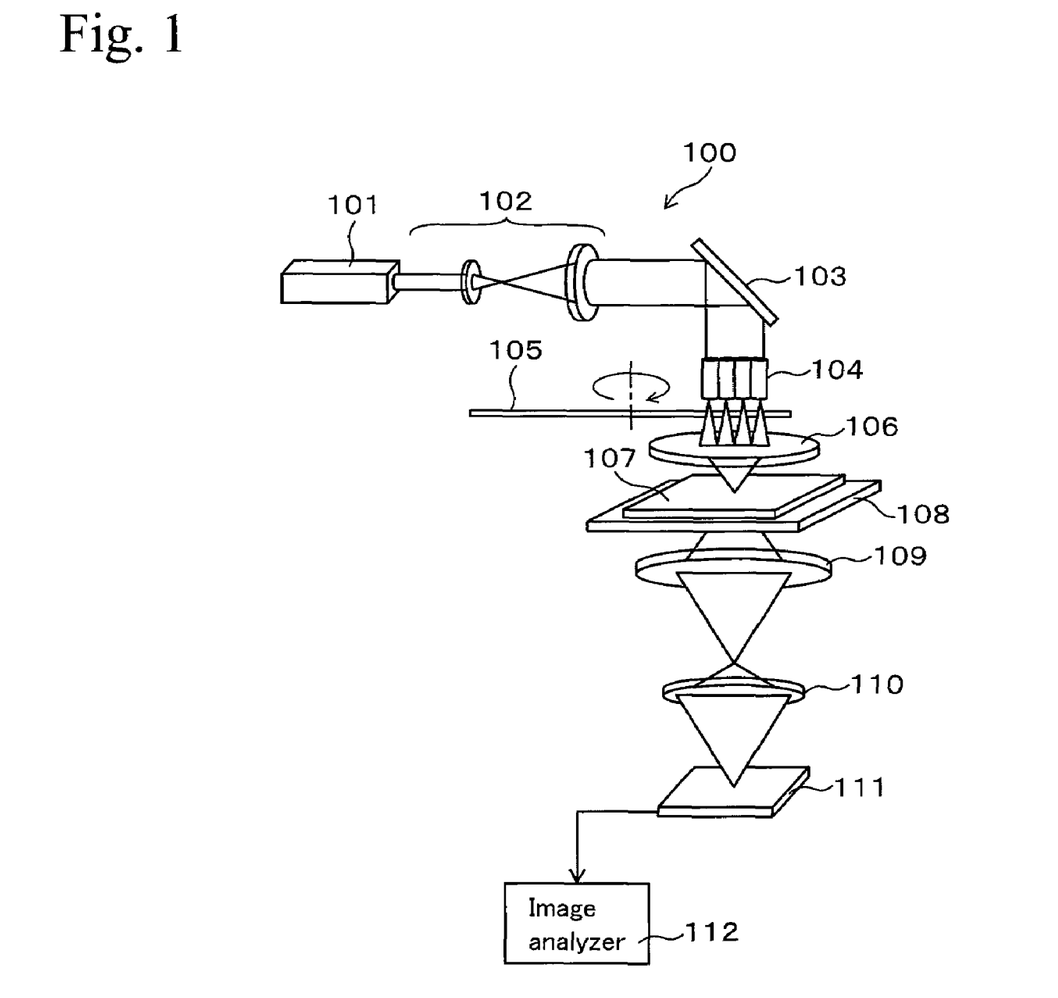
FIG. 1 is a schematic view showing an example of a photomask inspecting apparatus using the present invention.

In the first embodiment, an example of an optical apparatus (a photomask inspecting apparatus) for inspecting defects of an attenuated phase-shift mask is described. FIG. 1 is a schematic view showing an example of a photomask inspecting apparatus using the present invention.

FIG. 1 shows a photomask inspecting apparatus 100 having a CW oscillation type laser light generating device 101 as a laser light source. The laser light generating device 101 outputs a laser light in the ultraviolet. For example, a device, which continuously oscillates a second harmonic wave having a wavelength of 257 nm of an argon ion laser, may be used as the laser light generating device 101. Although the wavelength of the wave is not limited thereto, the wavelength is preferably the same as that of exposure light used for inspecting a photomask.

Laser light is output from the laser light generating device 101 and is shaped into a beam by a beam expander 102, and the beam enters a fly-eye lens 104 of an integrator via a reflecting mirror 103. The fly-eye lens 104 makes even the intensity distribution of the laser light. The fly-eye lens 104 is formed by arraying plural lenses so as to integrate them.

The laser light having passed through the fly-eye lens 104 passes through a rotating phase difference plate 105. The rotating phase difference plate 105 is a light transmissive circular plate in which plural micro areas having different depths (surface steps) are randomly provided on the surface, and the rotating phase difference plate 105 rotates by a motor (not shown in the figure). In this example, silica with high transmittance for a wavelength of 257 nm is used as a material of the rotating phase difference plate. The rotating phase difference plate 105 moderates temporal coherence of the laser light and decreases generation of interference due to the temporal coherence.

The laser light having passed through the rotating phase difference plate 105 is concentrated by a condenser lens 106, which is an example of a light focusing optical system of the present invention. The laser light concentrated by the condenser lens 106 is irradiated on a photomask 107 of an object to be inspected. In this example, an attenuated phase-shift mask is used as the photomask 107 of an object to be inspected. The photomask 107 is mounted on an X-Y stage 108. By moving the X-Y stage 108 within a plane perpendicular to the optical axis, the mask patterned area of the photomask can be observed in plural pieces.

Although not clearly shown in the figure, the X-Y stage 108 has an opening at a portion corresponding to an observation area, and the laser light having passed through the photomask 107 passes through the opening. The laser light having passed through the opening is concentrated by an objective lens 109 of an example of the projecting optical system of the present invention. Then, the laser light is appropriately magnified by a variable magnification optical system 110 and enters into an image sensor 111.

FIG. 1 simply shows the variable magnification optical system 110 as if the variable magnification optical system 110 consisted of one lens, but a practical variable magnification optical system may be made of a more complicated optical system. A sensor having a high-resolution CCD element is used as the image sensor 111.

The image sensor 111 is connected to an image analyzer 112. The image analyzer 112 has a function of analyzing images by software. Specifically, the image analyzer 112 has a memory and an image processing integrated circuit. The memory stores image data of a pattern of a photomask as a reference, and the image processing integrated circuit compares the reference image data stored in the memory and an image data of the photomask 107, which is captured by the image sensor 111. The comparison of the image data is performed by software, and thus data relating to the existence of defects, the positions of defects, and the states of defects in the mask pattern of the photomask are obtained.

Derivation of the Right Side Portion in the Numerical Formula (1)

A distribution of generation positions of ghost images in a two-dimensional plane is expressed by an image intensity distribution I(x, y) using degree of coherence. The image intensity distribution I(x, y) is expressed in the following numerical formula (3) by using a transmittance of an object; T=o(x, y) and an amplitude spread function of the projecting optical system; ASF(x, y).

$$I(x, y) = \quad (3)$$
$$C \int \int \int \int_{-\infty}^{\infty} dx_1 dy_1 dx_2 dy_2 \mu(x_1 - x_2, y_1 - y_2) o(x_1, y_1) o*(x_2, y_2) \times ASF(x - x_1, y - y_1) ASF*(x - x_2, y - y_2)$$

Accordingly, contrast of a ghost image is defined by ASF, the transmittance o of an object, and the degree μ of coherence. In a condition in which μ(x, y)=1, the contrast of a ghost image can be decreased as long as the distance between ($x_1$, $y_1$) and ($x_2$, $y_2$) is sufficiently large compared to the spread of ASF. Hereinafter, a derivation process of the inequality in the numerical formula (1) is described based on this idea.

ASF(x, y) in the above numeral formula (3) is expressed as the following numerical formula (4) by using Bessel function $J_1(x)$. In this case, k=2π/λ.

$$ASF(r) = 2J_1(kNAr)/kNAr \quad (4)$$

When r>>(λ/NA), that is, when ASF(r) is sufficiently small compared with peak amplitude, the Bessel function in the above numerical formula (4) is expressed as the following numerical formula (5) by approximate expansion.

$$J_1(x) \approx \sqrt{\frac{2}{\pi x}} \cdot \cos\left(x - \frac{3\pi}{4}\right) \quad (5)$$

By substituting the numerical formula (5) for the numerical formula (3), the following numerical formula (6) is obtained based on R=kNAr.

$$ASF(r) = 2J_1(R)/R = \frac{2\sqrt{\frac{2}{\pi R}} \cdot \cos\left(R - \frac{3\pi}{4}\right)}{R} \quad (6)$$

Degree of contrast, at which the effects of a ghost image are negligible, is expressed as γ, and ASF(R) is decreased to C with respect to the center value ASF(0) of ASF under a certain condition. In this condition, an amplitude transmittance of a light blocking portion of a mask is expressed as T, thereby forming γ=CT. In this case, the left side in the above numerical formula (6) is expressed as C, and both sides of the numerical formula (6) are squared and are arranged, whereby the following numerical formula (7) is obtained.

$$\frac{\pi C^2}{8} R^3 = \cos^2\left(R - \frac{3\pi}{4}\right) \quad (7)$$

When ASF(R) exhibits C with respect to ASF(0) at a position, the upper-side-envelope-curve ρ(r) of ASF(r) can be written as $$\rho(r) = \frac{2}{R} \sqrt{\frac{2}{\pi R}},$$

and the right side in the above numerical formula (7) is 1. Therefore, in this case, the following numerical formula (8) is derived from the numerical formula (7).

$$R = \sqrt[3]{\frac{8}{\pi C^2}} \quad (8)$$

Since R=kNAr, the numerical formula (8) is arranged by focusing on r, whereby the following numerical formula (9) is obtained.

$$r = \frac{\sqrt[3]{\frac{8}{\pi C^2}}}{kNA} \quad (9)$$

A generation position of a ghost image is expressed as r, and a position at which spatial coherence is intensified is expressed as (λ/p). In a condition in which the position r is at the outside of the position (λ/p), the following numerical formula (10) is obtained from the numerical formula (9).

$$\frac{\lambda}{p} \geq \frac{\sqrt[3]{\frac{8}{\pi C^2}}}{kNA} \qquad (10)$$

A luminescent spot distance of an integrator is defined by $p=(2 \times NA \times \sigma)/N$. Therefore, p is removed from the above numerical formula (10), and the numerical formula (10) is arranged by focusing on N and using the relationship of $k=2\pi/\lambda$, whereby the following numerical formula (1) is obtained. In this case, $C=\gamma/T$.

$$N \geq \sqrt[3]{\frac{8}{\pi C^2}} \quad (C = \gamma/T) \qquad (1)$$

Derivation of the Left Side Portion in the Numerical Formula (2)

Hereinafter, a basis of the inequality of the left side in the numerical formula (2) is described. The inequality of the left side in the numerical formula (2) defines a rough upper limit of a division number of an integrator.

Figure 2:
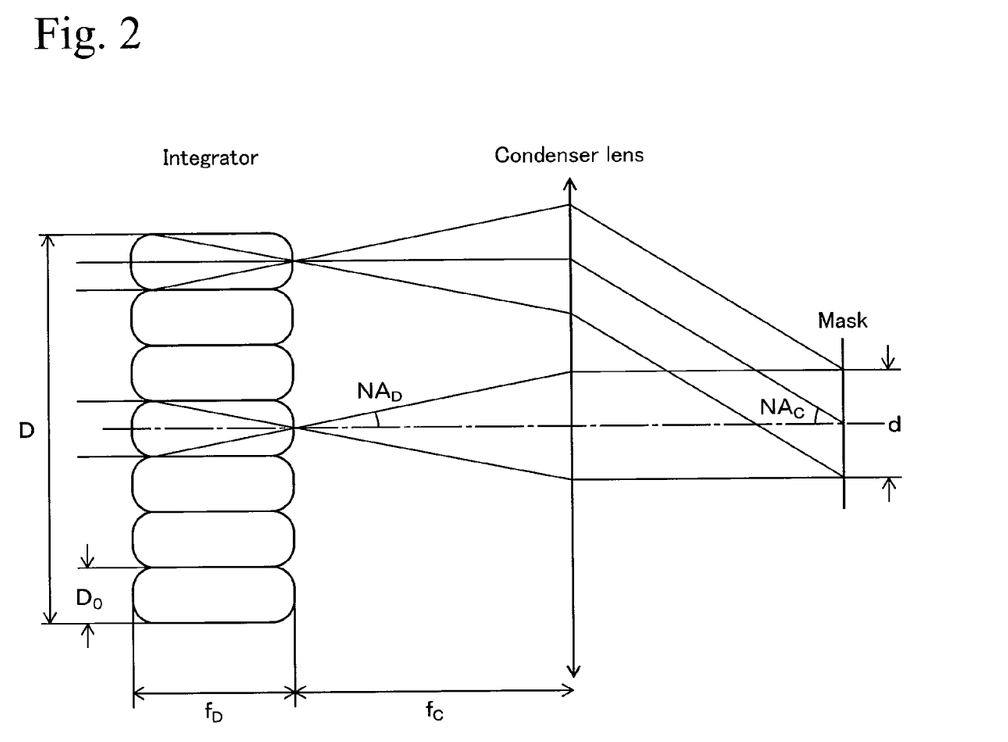
FIG. 2 schematically shows an optical model for describing a division number of an integrator.

FIG. 2 schematically shows an optical model for describing a division number of an integrator. FIG. 2 shows an optical model in a case in which an integrator is made of one layer.

FIG. 2 shows a microscope visual field d and a condenser lens having a numerical aperture $NA_C=NA\sigma$ and a focal length $f_C$. NA is a numerical aperture of an objective lens (not shown in FIG. 2) of the projecting system in the back side of a mask. FIG. 2 also shows integrator elements having a numerical aperture $NA_D$, a focal length $f_D$, and a diameter $D_0$, and the integrator element is one lens for forming the integrator. In this case, the number of the integrator elements (a division number) in a predetermined direction is expressed as N, $D=ND_0$.

The microscope visual field d is expressed as the following numerical formula (11) by using the focal length $f_C$ of the condenser lens, the focal length $f_D$, and the diameter $D_0$ of the integrator element.

$$d = D_0 \frac{f_C}{f_D} \qquad (11)$$

In order to have a generation position of a ghost at the outside of the microscope visual field, a condition of a number M of the integrator elements is defined by the following numerical formula (12). A derivation process of the numerical formula (12) will be described in relation to a numerical formula (19) that is described in the following reference example.

$$M > (2 \times d \times NA_c)/\lambda \qquad (12)$$

By substituting the numerical formula (11), $NA_C=D/2f_C$, and $D=ND_0$ for the numerical formula (12), the following numerical formula (13) is derived.

$$M > \frac{2}{\lambda} \times D_0 \frac{f_C}{f_D} \times \frac{D}{2f_C} = N \times \frac{D_0^2}{\lambda f_D} \qquad (13)$$

In this case, N is a number of the integrator elements in a predetermined direction, and M is a number of the integrator elements, which is necessary for having a generation position of a ghost at the outside of the microscope visual field. Accordingly, since N=M, a critical condition is obtained in order to satisfy the above numerical formula (13). That is, a condition for a division number of a practical integrator being greater than M is defined by the following numerical formula (14).

$$\frac{D_0^2}{\lambda f_D} < 1 \qquad (14)$$

On the other hand, in view of the Fresnel number of the integrator element, the following condition must be satisfied in order to form a spot having a diameter of not more than an incident light diameter at an end surface of output.

$$\frac{D_0^2}{4\lambda f_D} = Q \geq 1 \qquad (15)$$

When Q=1, the diameter of incident light flux equals the diameter of the spot. Therefore, the value of Q must be at least 1. That is, in order to effectively obtain the function of the integrator, a condition of $Q \geq 1$ must be satisfied in the numerical formula (15). If the value of Q is 1, $N \leq (M/4)$, and the maximum number of elements that can be included in an integrator of one layer is M/4. Therefore, the number N of elements (the division number N in a predetermined direction) of a practical integrator is set to be not more than ¼ of the number M of elements (the division number M in a predetermined direction) defined by the numerical formula (13). As a result, the effects of the integrator are obtained without deteriorating the function thereof.

The above description is generalized and is formulated hereinafter. First, since the value of N must be not more than ¼ of the value of M, N is expressed as the following numerical formula (16) by using M.

$$N \leq M/4 \qquad (16)$$

Ghosts are acceptable as long as the intensity (contrast) of the ghosts are lower than an upper limit, even when the ghosts are generated in a visual field. As a critical condition of the upper limit, the condition of the numerical formula (12) is used. In this condition, ghosts are acceptable as long as generation positions of principal maximums of the ghosts are outside of the visual field.

That is, a distribution of generation positions of ghost images in a two-dimensional plane is expressed by the numerical formula (3). As can be understood from the characteristic of the Bessel function, contrast of a ghost image shown by the numerical formula (3) is reduced as the generation position of the ghost image is separated from a real image. In other words, as the ghost image is separated from the real image, the degree of interference is decreased, whereby the contrast of the ghost image due to the interference is reduced.

When at least a ghost image is positioned at the outside of the effective visual field and is separated from a real image, the degree of interference is sufficiently small, and the effects of the ghost image may be negligible. The condition in this case is used as a condition for M in the above numerical formula (16). In this case, a critical value of a lower limit of M is derived from the numerical formula (12) and is defined as $M=(2\times d\times NA_C)/\lambda$. Therefore, the numerical formula (16) is modified into the following numerical formula (17).

$$N \leq (2\times d\times NA_C)/(4\times \lambda) \qquad (17)$$

Although the numerical formula (17) is derived based on Q=1 as a critical value, a condition of Q≧1 is practically used. As is clearly shown by the relationship expression of M≧N× 4Q (or N≦(M/4Q)) derived from the numerical formula (13) and the numerical formula (15), the maximum value of N with respect to the value of M is inversely proportional to the value of Q and is smaller. Accordingly, in view of this, the above numerical formula (17) is modified into the following numerical formula (18) based on $Q=D^2/(4\lambda f_D)$ (Q≧1).

$$N \leq (2\times d\times NA_C)/(4\times \lambda \times Q) \qquad (18)$$

$NA_C$ can be expressed as $NA_C=NA\sigma$ based on NA as a numerical aperture of the objective lens of the projecting system (not shown in FIG. 2) in the back side of the mask. By expressing NA as a numerical aperture $NA_2$ of a projecting optical system, an expression of $NA_C=NA_2\sigma$ is obtained, and the above numerical formula (18) is the same as the left side portion in the numerical formula (2). Thus, a numerical formula for defining an upper limit of a division number N of an integrator is derived, and the numerical formula is used when Q≧1 is satisfied.

In a case of obtaining a necessary division number by serially arranging plural integrators, the following steps are used. First, an optical design is performed by assuming use of one integrator, and an upper limit of a division number N of the integrator is calculated by using the inequality in the left side of the numerical formula (2). Then, a division number N satisfying the above numerical formula (2) is selected within the upper limit, and a combination of plural integrators is selected so as to obtain a division number for satisfying the division number N.

Specific Example

In the numerical formula (1), contrast γ of a ghost image is set at 0.1% (0.001), for example. In addition, an amplitude transmittance T of a mask is set at 1.0. In this case, if the value of NA of the objective lens 109 of the projecting optical system is 0.1% (0.001), and the value of a coherence factor σ is 1.0, N≧43.5 is derived from the numerical formula (1). Therefore, by using an integrator with not less than 44×44 divisions, ghost images occurring within an effective visual field have contrast of not more than 0.1%. If T=√29%, by using an integrator with not less than 29×29 divisions, ghost images occurring within an effective visual field have a contrast of not more than 0.1%.

Results of Numerical Calculations

Hereinafter, the usefulness of the numerical formula (1) was verified by numerical calculations, and the results are described. In this case, as a prior condition, in addition to the conditions in the above specific example, an effective visual field was set to have a 15 μm square rectangular shape, and a wavelength λ of laser light output from the laser light generating device 101 was set at 257 nm. Moreover, a value of NA of the objective lens 109 of the projecting optical system was set at 0.75, and a coherence factor σ was set at 1.0. A predetermined amount of photomask designed for exposure light having a wavelength of 193 nm was used. Since the apparatus for inspecting defects of a mask has an expanding optical system, an incident angle to the image sensor was assumed to be extremely small. Calculation of a diffraction field was performed based on a model of transmission between irises using scalar approximation excluding effects of polarized light. The calculation was performed excluding Fresnel number.

Figure 5A:
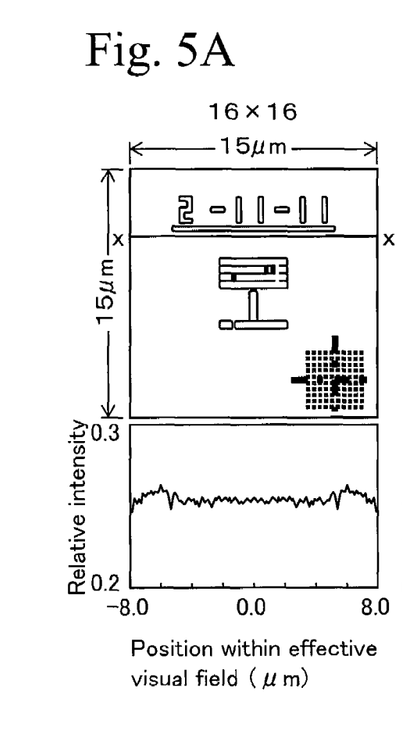
FIGS. 5A to 5D show calculated results.
Figure 5B:
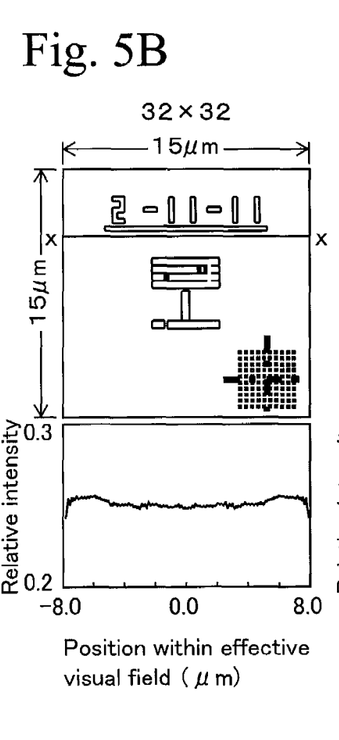
Figure 5C:
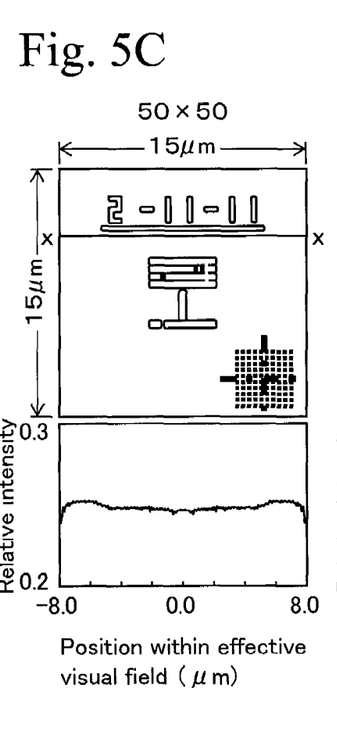
Figure 5D:
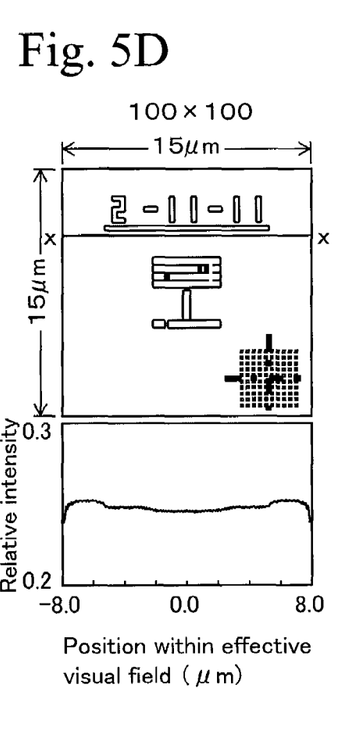

FIGS. 5A to 5D show results of numerical calculations. The effective visual field having a rectangular shape is shown in each of the upper sides of FIGS. 5A to 5D, and an intensity distribution of detected light on a line X-X crossing the effective visual field is shown in each of the lower sides of FIGS. 5A to 5D. FIG. 5A shows a calculated result in a case of an integrator having a division number of 16×16. FIG. 5B shows a calculated result in a case of an integrator having a division number of 32×32. FIG. 5C shows a calculated result in a case of an integrator having a division number of 50×50. FIG. 5D shows a calculated result in a case of an integrator having a division number of 100×100.

FIG. 5A corresponds to a case of using N=16 as N in the numerical formula (1), FIG. 5B corresponds to a case of using N=32 as N in the numerical formula (1), FIG. 5C corresponds to a case of using N=50 as N in the numerical formula (1), and FIG. 5D corresponds to a case of using N=100 as N in the numerical formula (1).

As is clearly shown in FIGS. 5A to 5D, evenness of the intensity distribution is improved as N is increased. This indicates that interference is decreased, that is, the intensity of ghost images is decreased, as N is increased. In the case of N=50 in FIG. 5C, interference that may cause ghost images is recognized, although the amount of interference is small. In the case of N=100 in FIG. 5D, the intensity is increased at the peripheries, and the intensity distribution is uneven, but interference that may cause ghost images is not seen. As can be understood from FIGS. 5A to 5D, as the number N of the integrator is increased, small unevenness of the intensity distribution is improved, and intensity distribution of light transmitted through the photomask becomes flat.

As described above, in a condition in which σ=1.0, γ=0.001, and T=1.0 (C=0.001), the range of N obtained from the numerical formula (1) is N≧43.5. This result corresponds to the calculated results in the cases of N=50 and N=100 in FIGS. 5C and 5D, in which the unevenness of the relative intensity distribution is superior. Accordingly, the numerical formula (1) and the right side of the numerical formula (2) are appropriate.

Change in Ghost Image Depending on Inspecting Wavelength

Hereinafter, changes in a ghost image depending on differences in the wavelength of inspection laser light to be irradiated are described. In general, an attenuated phase shift mask is designed according to the wavelength of exposure light. This is because the attenuating amount of a masked area varies according to a wavelength of the exposure light. Therefore, in order to maximally obtain the optical function of the attenuated phase shift mask as a photomask, an optical design must be performed according to a wavelength of the exposure light.

Figure 6A:
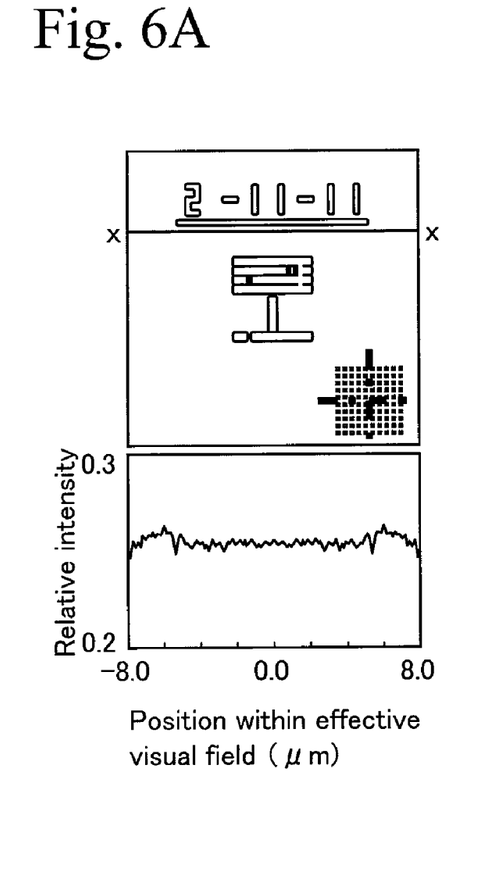
FIGS. 6A and 6B show calculated results.
Figure 6B:
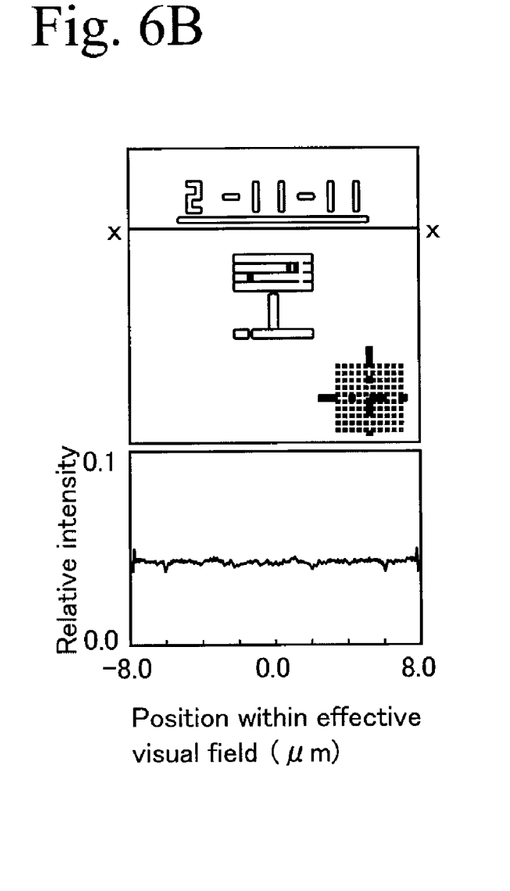

FIGS. 6A and 6B show results of calculating a generation condition of interference by changing the inspecting wavelength. In conditions for obtaining the calculated results in FIGS. 6A and 6B, an effective visual field was set to have a 15 μm square rectangular shape, a value of NA of the objective lens 109 of the projecting optical system was set at 0.75, and a coherence factor σ was set at 1.0. A wavelength λ of laser light output from the laser light generating device 101 was set at 257 nm in the case of FIG. 6A and was set at 193 nm in the case of FIG. 6B. A predetermined amount of photomask designed for exposure light having a wavelength of 193 nm was used.

As is clearly shown in FIGS. 6A and 6B, by corresponding the inspecting wavelength with the wavelength of exposure light, interference is reduced, and generation of ghost images is reduced. In addition, an intensity distribution of light transmitted through the photomask becomes flat. This indicates that unevenness of distribution of irradiation intensity of the exposure light to be irradiated on the photomask is improved.

The results shown in FIGS. 6A and 6B may be due to the following reason. That is, the attenuated phase shift mask used in the calculation is designed for an exposure wavelength of 193 nm and has a transmittance of 6% with respect to a wavelength of 193 nm in a masked area (a light blocking area). On the other hand, the transmittance is 29% with respect to a wavelength of 257 nm in the same area. As a result, effects of light transmitted through the masked area are large in the case of FIG. 6A, whereby strong interference is generated.

The effects of the difference between the inspecting wavelength and the exposure wavelength may greatly increase in an EUV mask defect inspection using ultra short wavelength light having a wavelength of 13.5 nm, which is currently under development. When an EUV mask is observed by a mask defect inspecting apparatus using a deep ultraviolet light source, only a reflected image with low contrast is obtained due to the difference of optical constant. When the difference of contrast between a light blocking portion and a transparent portion is small, ghost images occur more often, and therefore, the difference between the inspecting wavelength and the exposure wavelength are important for a binary mask (a black and white mask).

(2) Second Embodiment

The optical apparatus shown in FIG. 1 may be used for an exposure apparatus using a laser light source. In this case, an X-Y stage is placed at the position of the image sensor 111, and a sample to be exposed is arranged on the stage, whereby the sample is exposed. The variable magnification optical system 110 is changed to a demagnifying optical system, so that a pattern of a photomask is reduced in size and is irradiated on the sample.

In a case of using the apparatus in FIG. 1 for an exposure apparatus, when an attenuated phase shift mask is used as a photomask, ghost images occur in an exposed area (an area illuminated with laser light), but the contrast of the ghost images can be sufficiently small for the reason described in the first embodiment. Therefore, the generation of defects due to effects of ghost images is prevented in an exposure step. Since uneven distribution of irradiation intensity of exposure light to be irradiated on a photomask is improved, more uniform exposure can be performed.

(3) Variation of Embodiment

As a method for obtaining effects equivalent to those of increasing the division number of an integrator, besides a method of serially stacking integrators, a method of using plural light sources that emit light entering into an integrator may be used. In this case, output portions (output optical systems) of plural laser oscillating devices are put together and are placed at the position of the laser light generating device 101, and beams emitted from the laser oscillating devices are overlapped and are emitted to the integrator 104 via an appropriate optical system.

In this case, for example, if the number of the laser light sources is 2×2=4, and the number of the integrators is 4×4=16, the division number is 4×16=64, and optical effects are obtained. The optical effects are the same as those in a case in which a beam of light consisting of one light flux output from one laser oscillating device is passed through an integrator of 8×8=64.

(4) Reference Example

Hereinafter, as an idea relating to the present invention, an idea for removing effects of ghost images by forming the ghost images outside of an effective visual field is described. In this idea, an optical apparatus includes a laser light source for emitting a beam of light, an integrator for dividing the beam of light into plural beams of light, and a light focusing optical system for focusing the beams of light passed through the integrator. This optical apparatus also includes a stage, on which the light concentrated by the light focusing optical system is irradiated and on which an object may be placed, and includes a projecting optical system for projecting the light transmitted through the object. The following conditions satisfy the following numerical formula (19). The projecting optical system has a visual field including an effective visual field, and the integrator has a division number M corresponding to a predetermined direction in a predetermined effective visual field. The effective visual field has a size d in the predetermined direction. The light focusing optical system has numerical aperture $NA_1$, the projecting optical system has numerical aperture $NA_2$, and $(NA_1/NA_2)$ defines a coherence factor σ. The light emitted from the laser light source has a wavelength λ.

$$M > (2 \times d \times NA_2 \times \sigma)/\lambda \qquad (19)$$

According to the above-described structure, even when a ghost image is formed in a predetermined direction crossing the effective visual field, the position of the ghost image is at the outside of the effective visual field. Therefore, negative effects of ghost images on an illuminated surface, which occur when laser light having a high coherency is used as a light source, is avoided. According to this structure, for the same reason described in connection with the first aspect of the present invention, a luminance distribution of the laser light in the effective visual field is made even, and the evenness of an intensity distribution is improved.

The value of the right side of the numerical formula (3) is greater than the value of the left side of the numerical formula (2). Accordingly, effects at boundaries of integrator elements are not negligible. As a device for avoiding the effects of the boundaries of elements, a microlens array may be used, and the microlens array must be arranged so that numerical aperture of each integrator element is not changed. Other functions in the above structure are the same as those described in connection with the aspects of the present invention.

The right side of the inequality of the numerical formula (19) indicates a critical value of a condition in which a distance between a real image and a ghost image is larger than the size of the effective visual field. By defining M>(d×2×NA×σ)/λ, a ghost image emerges outside of the effective visual field containing the real image. That is, the ghost image can be made so that it is not visible in the visual field. A derivation process of the inequality of the numerical formula (19) will be described below in detail.

Figure 3:
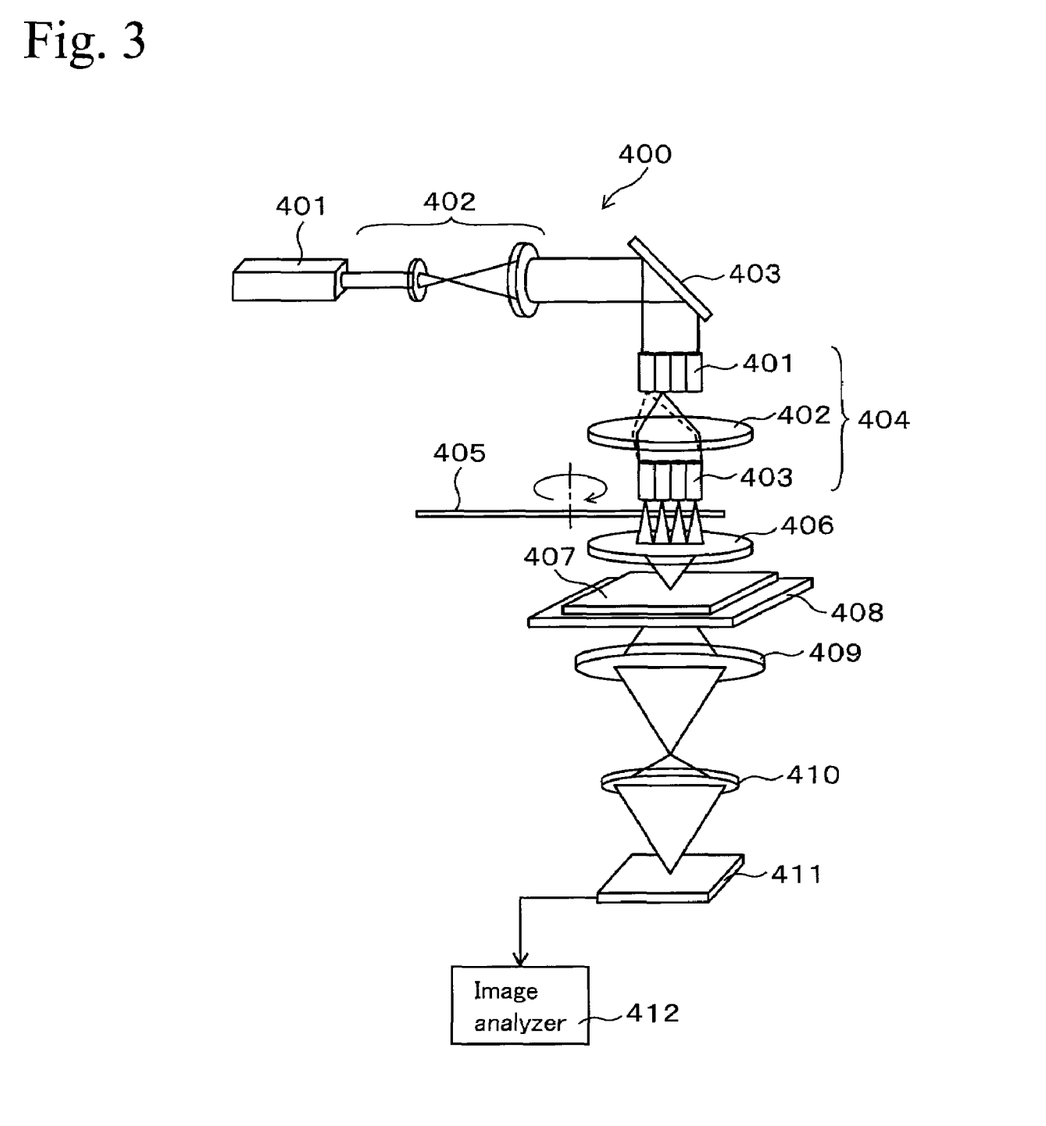
FIG. 3 is a schematic view showing another example of a photomask inspecting apparatus as a reference example.

Hereinafter, an example of an optical apparatus (a photomask inspecting apparatus) for inspecting defects of an attenuated phase shift mask is described as a reference example of an apparatus using the above structure. FIG. 3 is a schematic view of a photomask inspecting apparatus 400 exhibited as a reference example. The photomask inspecting apparatus 400 shown in FIG. 3 is different from the apparatus shown in FIG. 1 and has a double integrator structure instead of the fly-eye lens 104 of the apparatus shown in FIG. 1. Microlens arrays made of quartz are used for the integrator. In this case, other devices are the same as those in the photomask inspecting apparatus 100 shown in FIG. 1.

A double integrator is an integrator that may be formed by serially arranging two integrators on an optical axis in order to increase a division number. In this example, as shown in FIG. 3, a double integrator optical system 404 is formed by arranging a microlens array 401, an objective lens 402, and a microlens array 403, in that order, from a light source side. In this example, the microlens array 401 and the microlens array 402 are the same. Each lens of the microlens array 401 outputs a beam, and the objective lens 402 irradiates the beams on the entirety of the microlens array 403.

For example, by stacking integrators having a division number of 4×4=16 into two layers, optical functions are obtained, and the optical functions are equivalent to those in a case of using an integrator having a function of 16×16=256 divisions.

In this embodiment, a division number M satisfying the right side of the numerical formula (19) is secured by using a double integrator. The division number M of the integrator has a limit in view of the production cost, whereby the division numbers of the microlens arrays 401 and 403 must be set in view of this. Although an example of an integrator having a two-layered structure is shown in FIG. 3, a predetermined division number may be obtained by using a structure with three or more layers.

Other devices, such as a laser light generating device 401, a beam expander 402, a reflective mirror 403, a rotating phase plate 405, a photomask 407, an X-Y stage 408, an objective lens 409, a variable magnification optical system 410, an image sensor 411, and an image analyzer 412, are the same as those in the case of FIG. 1, and therefore, descriptions thereof are omitted.

Derivation of Numerical Formula (19)

Figure 4:
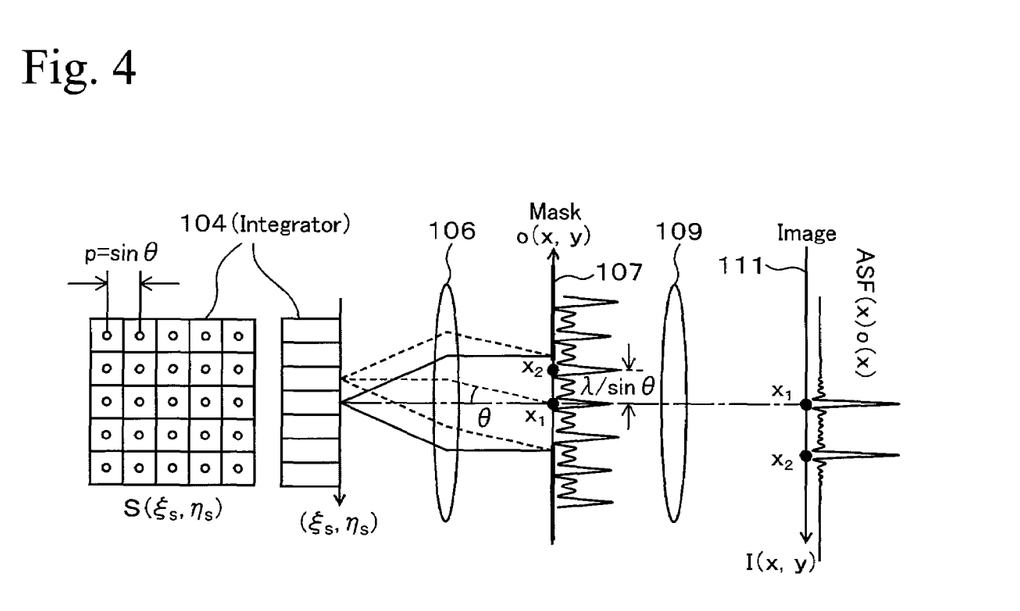
FIG. 4 schematically shows an optical model for describing the generation function of a ghost image.

A derivation process of the numerical formula (19) and a generation function of a ghost image related thereto are described hereinafter. First, an optical model shown in FIG. 4 is described as a model in which the optical system of the photomask inspecting apparatus shown in FIG. 1 is simplified. That is, the integrator 104 is used as a light source, and a model is assumed that luminescent points are aligned on the light source at N×N points at equal intervals and at equal intensity according to the arrangement of the integrator.

FIG. 4 schematically shows a condition in which light is irradiated on the photomask 107 of an attenuated phase shift mask and interferes at the output side (a surface opposite to the incidence surface of light), and the output light is concentrated by the objective lens 109 and is projected on a light-receiving surface of the image sensor 111. In this condition, a real image is formed at a coordinate $x_1$, and an image is formed at a coordinate $x_2$.

In this model, spatial coherence occurs on the surface of the photomask 107 by the periodicity of the integrator 104, and the spatial coherence is used as a cause of generation of a ghost image. The spatial coherence on the surface of the photomask 107 may be expressed as a degree of coherence $\mu(x, y)$. In this case, $\mu(x, y)$ is expressed by the following numerical formula (20) as a Fourier transformation of a distribution $S(\xi_S, \eta_S)$ of an illuminating light source using the Van Cittert-Zernike theorem.

$$\mu(x_1 - x_2, y_1 - y_2) \equiv \frac{\int\int d\xi_S d\eta_S S(\xi_S, \eta_S) \exp\left\{ik\left[\begin{array}{c}\xi_S(x_1 - x_2) +\\ \eta_S(y_1 - y_2)\end{array}\right]\right\}}{\int\int d\xi_S d\eta_S S(\xi_S, \eta_S)} \quad (20)$$

In this case, $k=2\pi/\lambda$, and iris coordinates $\xi_S$ and $\eta_S$ are direction cosines of light. In addition, $\lambda$ is a wavelength of laser light used in observation. By standardizing a total intensity sum of the light source (the integrator) 104 to be 1, the above numerical formula (20) is modified into the following numerical formula (21).

$$\mu(x_1 - x_2, y_1 - y_2) \equiv \frac{\sin\left(\frac{k}{2}Np(x_1 - x_2)\right)}{\sin\left(\frac{k}{2}p(x_1 - x_2)\right)} \quad (21)$$

$$\frac{\sin\left(\frac{k}{2}Np(y_1 - y_2)\right)}{\sin\left(\frac{k}{2}p(y_1 - y_2)\right)} \exp\{ik[\xi_O(x_1 - x_2) + \eta_O(y_1 - y_2)]\}$$

In this case, $\xi_O$ and $\eta_O$ are central coordinates of the integrator 104, and p is a value of a luminescent spot distance of the integrator in terms of direction cosine of incident light to the illuminated surface. In addition, p is a difference of the incident direction cosines of lights to the illuminated surface, and the lights are emitted from positions that are separated from each other by a luminescent spot distance $p_C$ of the integrator. If a focal distance of the light focusing optical system between the integrator and the illuminated surface is expressed as $f_C$, p is expressed as $(p_C/f_C)$.

In the numerical formula (21), interference between two points on the photomask 107 due to the spatial coherence is greatest, that is, a spatial coherence between two points is maximal under a certain condition. This condition is obtained by the following numerical formula (22) using m and n as an integral number.

$$(x_1-x_2)=\lambda/p \times m (y_1-y_2)=\lambda/p \times n \quad (22)$$

When the above numerical formula (22) is satisfied, as shown in FIG. 4, a high interference is generated by compositions transmitted through the photomask 107, whereby a real image is formed at a coordinate $x_1$ and an image is formed at a coordinate $x_2$ on the light-receiving surface of the image sensor 111. The numerical formula (22) indicates that a ghost image is periodically formed at a predetermined position. In other words, the numerical formula (22) is a formula indicating a generation position of a ghost image.

As can be understood from the numerical formula (22), a distance between interference images (ghost images), that is, a distance between a real image and a ghost image varies according to a wavelength $\lambda$ of laser light to be used and p. In this case, p includes variable numbers relating to the integrator 104 and the condenser lens 106 of the light focusing optical system. Therefore, by adjusting the variable numbers relating to the integrator 104 and the condenser lens 106 of the light focusing optical system, the distance between a real image and a ghost image indicated by the numerical formula (22) is controlled.

In inspection of defects of a photomask, problems caused by a ghost image do not occur as long as the ghost image is generated outside of the observation field, even when a ghost image is generated. In order to use this technical idea, a condition is selected in the above numerical formula (22) so that a ghost image is not formed within an observation area.

The variable number p is a value of a luminescent spot distance of an integrator in terms of direction cosine of incident light to an illuminated surface. The variable number p is expressed as the following numerical formula (23) by using a division number of the integrator in a direction of the luminescent spot distance as M.

$$p=(2 \times NA_2 \times \sigma)/M \qquad (23)$$

The image sensor 111 has a field to be observed (an effective visual field), and a size in the field in a direction of the above luminescent spot distance is set to be d. The effects of a ghost image can be removed on condition that a real image is observed in the range of d and that the ghost image is formed outside of the range of d. When this function is expressed by using the numerical formula (22), the following numerical formula (24) is derived.

$$d < \lambda/p \qquad (24)$$

By eliminating p from the numerical formula (23) and from the numerical formula (24), the following numerical formula (19) is obtained.

$$M > (2 \times d \times NA_2 \times \sigma)/\lambda \qquad (19)$$

Thus, the numerical formula (19) is derived. In the numerical formula (19), a division number M of the integrator in an objective direction is set within the effective visual field so as to satisfy the numerical formula (19). As a result, a ghost image generated in the objective direction is formed outside of the effective visual field. By using a relationship of $NA_C = NA_2 \sigma$ in the numerical formula (19), the numerical formula (12) is obtained.

Specific Example

An example of an optical design satisfying the numerical formula (19) is described with reference to a specific example hereinafter. In this example, the effective visual field to be observed has a length d=100 μm in a predetermined direction, a wavelength λ of laser light output from the laser light generating device 101 is set at 250 nm, a value of NA of the objective lens 109 of the projecting optical system is set at 0.75, and a coherence factor σ is set at 1.0. In this case, the right side of the numerical formula (2) is 600. That is, in the above condition, M>600 must be satisfied in order not to form a ghost image on a line of the length d of 100 μm.

In order to satisfy this condition, microlens arrays having a division number of 25×25 are used as the microlens arrays 401 and 403, in the structure shown in FIG. 3. Accordingly, M=625 in the shortest direction crossing the effective visual field, whereby the condition of M>600 is satisfied, and a ghost image is not generated within the effective visual field. This condition does not satisfy the above-described condition of the upper limit of the number of the integrator, and is thereby appropriately used when the Fresnel number is not included. In this example, by using microlens arrays, the integrator structure is formed excluding the Fresnel number.

As a structure excluding the Fresnel number, a case of not using an integrator may be mentioned, and in this case, light sources are prepared as much as the number of M, which is calculated from the numerical formula (19).

The present invention may be used for apparatuses for inspecting photomasks used in photolithography processes. In addition, the present invention may be used for exposure apparatuses used in photolithography processes.

What is claimed is:

1. An optical apparatus comprising:
   a laser light source for emitting a beam of light;
   an integrator for dividing the beam of light into plural beams of light;
   a light focusing optical system for focusing the beams of light passed through the integrator;
   a stage on which the light concentrated by the light focusing optical system is irradiated and on which an object may be placed; and
   a projecting optical system for projecting the light transmitted through the object,
   wherein the projecting optical system has a visual field including an effective visual field, the integrator has a division number N corresponding to a predetermined direction in a predetermined effective visual field, a ghost image is formed in the effective visual field in the predetermined direction and has contrast γ, the light focusing optical system has numerical aperture $NA_1$, the projecting optical system has numerical aperture $NA_2$, $(NA_1/NA_2)$ defines a coherence factor σ, and the object has a light blocking portion with an amplitude transmittance T such that C is the ratio of the contrast γ to the amplitude transmittance T, whereby the following numerical formula (1) is satisfied $$N \geq \frac{\sigma}{\pi} \sqrt[3]{\frac{8}{\pi C^2}} \quad (C = \gamma/T). \qquad (1)$$

2. The optical apparatus according to claim 1, wherein the integrator has an aperture size D and a focal length f, and the light passing through the integrator has a wavelength λ, a Fresnel number Q is defined as $D^2/(4\lambda f) = Q$ ($Q \geq 1$), and the effective visual field has a size d in the predetermined direction, whereby the following numerical formula (2) is satisfied $$(2 \times d \times NA_2 \times \sigma)/(4 \times \lambda \times Q) \geq N \geq \frac{\sigma}{\pi} \sqrt[3]{\frac{8}{\pi C^2}}. \qquad (2)$$

3. A photomask inspecting apparatus comprising the structure of the optical apparatus recited in claim 1.

4. An exposure apparatus comprising the structure of the optical apparatus recited in claim 1.

* * * * *